US006126375A

United States Patent [19]

O'Brien

[11] Patent Number: 6,126,375

[45] Date of Patent: Oct. 3, 2000

[54] MATERIAL TESTING APPARATUS

[76] Inventor: Jack O'Brien, 6 Chenango La., Binghamton, N.Y. 13901

[21] Appl. No.: 09/387,924

[22] Filed: Sep. 1, 1999

Related U.S. Application Data

[60] Provisional application No. 60/100,314, Sep. 15, 1998.

[51] Int. Cl.[7] .................... B65G 65/30

[52] U.S. Cl. .................... 414/299; 141/240; 222/485; 414/328; 73/863.41

[58] Field of Search .................... 414/299, 328; 141/237, 240; 222/185.1, 485; 73/863.41

[56] References Cited

U.S. PATENT DOCUMENTS

| | | | |
|---|---|---|---|
| 1,795,987 | 3/1931 | Adams | 414/299 |
| 2,593,535 | 4/1952 | Cannon, Jr. | 414/299 X |
| 4,039,062 | 8/1977 | Carre et al. | 222/485 X |
| 4,265,065 | 5/1981 | Osada | 222/485 X |
| 4,553,617 | 11/1985 | Tatematsu | 222/485 X |

FOREIGN PATENT DOCUMENTS

| | | | |
|---|---|---|---|
| 5286576 | 11/1993 | Japan | 414/328 |

*Primary Examiner*—Steven A. Bratlie
*Attorney, Agent, or Firm*—Salzman & Levy

[57] ABSTRACT

The invention consists of a hopper to place material in, and a door beneath it to hold back the material until it is to be released onto a grid consisting of four separate compartments or chutes that direct the material into four separate sample containers. The latch is arranged in such a manner as to allow the gates to open suddenly, and simultaneously, releasing the material in a mass (rather than slowly), assuring an even flow of the material down the chutes and into the four waiting containers below. This assures an unbiased sample in each container. For further reductions in sample size, the common practice is to choose any two opposite corner containers, combine in the hopper and repeat the process.

16 Claims, 2 Drawing Sheets

MATERIAL TESTING APPARATUS

This application claims benefit of Provisional Application 60/100,314 filed Sep. 15, 1998.

FIELD OF THE INVENTION

The invention relates to road construction methods and apparatuses and, more particularly, to a device for dividing large samples of particulate material into representative, smaller, separate parts, regardless of the stickiness of the sample material, such an apparatus being most useful in road construction for preparing a sample of hot asphalt for testing.

BACKGROUND OF THE INVENTION

Road construction is an art having its roots in antiquity. Modern road building techniques involve the use of large earth, cement, and asphalt handling vehicles. Despite the many advances in road building machinery, some of the techniques for testing materials in the field remain cumbersome and old fashioned.

One method for testing earth compaction is called the Ottawa sand test, wherein a fine sand is poured from a bottle into a hole from which foundation soil has been removed by the use of a large spoon. The weight of the Ottawa sand that fills the hole is determined by weighing the remaining Ottawa sand in the bottle, and then subtracting that weight from the entire sand and bottle weight. The sand weight that fills the hole is then compared to that of the removed soil. Compaction and moisture calculations can then be made for the foundation soil.

Another road building method involves taking a small sample portion of a large batch of hot asphalt for testing purposes. The batch of hot asphalt is first sampled from the haul unit or sampling device using metal buckets. Then, it is poured on a tray and spread evenly in a pan. Next, a spatula or blade is used to divide the material down the middle vertically and then horizontally, forming a plus sign in the material. Next, two opposing corners of the sample are removed using a scoop and spatula. The remaining asphalt is then used as a test sample.

This technique does not provide an accurate sample, because the material tends to segregate and cool down when handled in this manner. For testing purposes, the sample then requires reheating, resulting in lost time and the inconvenience of additional procedural steps. It has occurred to some that splitter-type machines might be used to quarter asphalt, but this is not possible, owing to the tacky nature of the asphalt.

The present invention has developed a machine for obtaining a hot mix asphalt sample that will not segregate or require reheating. The machine of this invention can quickly reduce even sticky asphalt to the correct size for testing.

The inventive apparatus for volumetrically testing these materials must conform to the procedures and specifications outlined and defined in the manual for the American Association of State Highway and Transportation Officials, or AASHTO (444 North Capitol Street, N.W., Suite 249, Washington, D.C. 20001).

SUMMARY OF THE INVENTION

In accordance with the present invention, there is provided a device for quickly obtaining a test sample from a batch of particulate material. The device comprises a funnel, a hopper disposed directly beneath the funnel, four chutes located below the hopper, which provide a grid configuration, and four sampling buckets arranged beneath the chutes. The batch of particulate material is poured into the funnel, which directs the material towards the center thereof. The centering of the material assures that an even distribution of the material is presented to the hopper. Gates located in the bottom of the hopper are then opened to allow the material to fall upon the grid formed by the four chutes located below the hopper. The material passes from the hopper into the grid, and is evenly distributed into the four awaiting buckets. Reduction of the hot asphalt mix, or any other batch of particulate material, is accomplished quickly by the device, while closely duplicating the approved AASHTO procedure.

It is an object of this invention to provide an apparatus for separating a large particulate batch into smaller test samples.

It is another object of the invention to provide an apparatus that will quickly obtain a sample from a large particulate batch of material.

BRIEF DESCRIPTION OF THE DRAWINGS

A complete understanding of the present invention may be obtained by reference to the accompanying drawings, when considered in conjunction with the subsequent detailed description, in which.

For purposes of clarity and brevity, like elements and components of the device of this invention will bear the same numbering and designations throughout the figures.

DESCRIPTION OF THE PREFERRED EMBODIMENT

Figure 1:
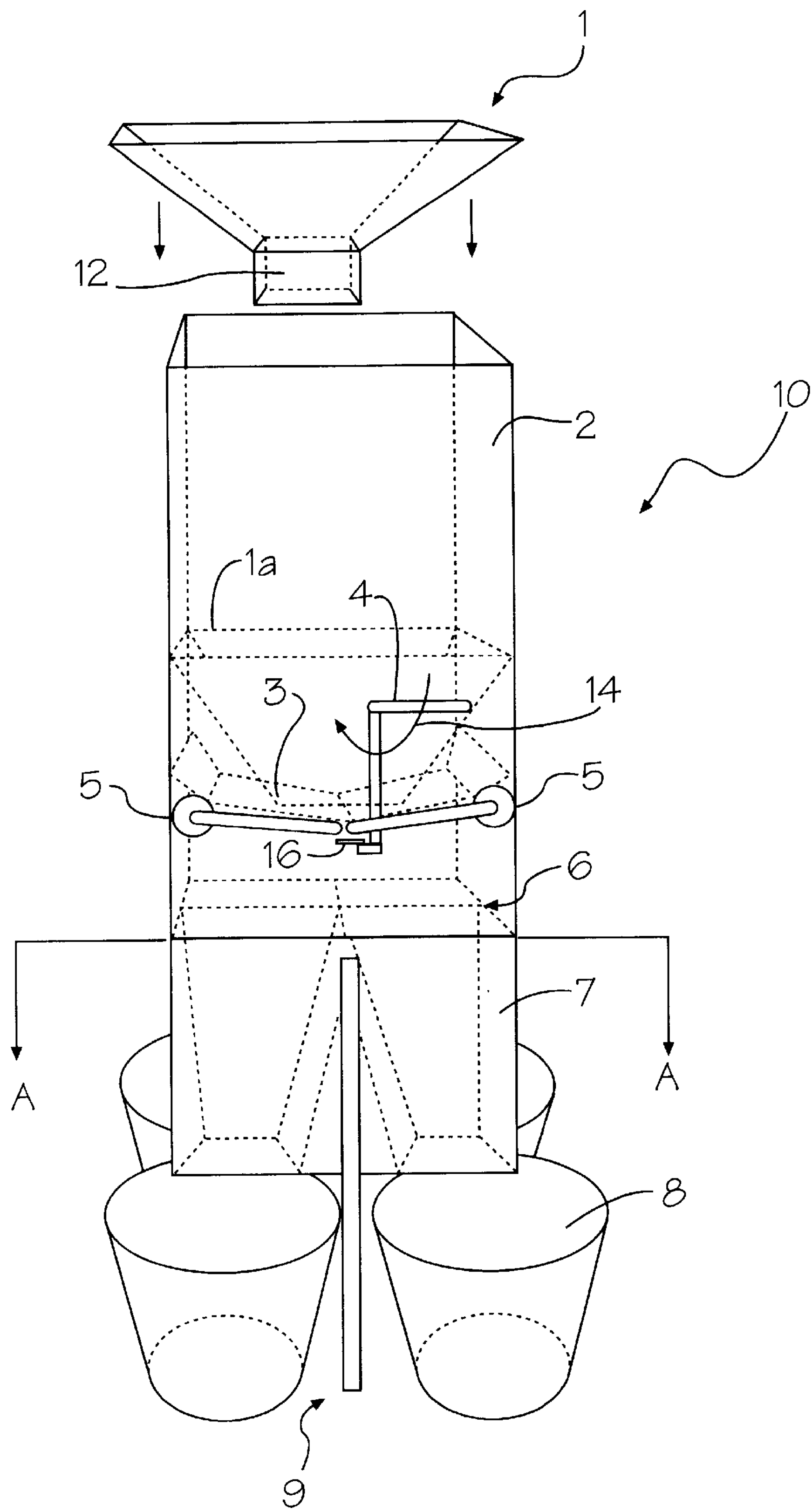
FIG. 1 illustrates a front, perspective view of the apparatus of this invention.

Generally speaking, the invention features a device for quickly obtaining a test sample from a batch of particulate material. The device comprises a funnel, a hopper disposed directly beneath the funnel, four chutes located below the hopper, which provide a grid configuration, and four sampling buckets arranged beneath the chutes. The batch of particulate material is poured into the funnel, which directs the material toward the four buckets disposed below. The material passing into each bucket of the device is one-fourth of the batch of material entering the hopper.

Sampling Procedure

The method of obtaining a particulate sample is described in "AASHTO T 168 Sampling Bituminous Paving Mixtures", summarized as follows:

1. Randomly select at least three areas of approximately equal size from a conveyor belt, roadway prior to compaction, funnel device feeding a conveyor for mixture delivery to storage, roadway after compaction, or truck transports or paver hopper, and combine to form a field sample whose quantity equals or exceeds the minimum recommended in §4.3.2. of ASTM D 979-89.

The Specification from ASTM D 979 §4.3.2 is as follows:

§4.3.2 A guide to the quantity of material in field samples is given in Table I, below. The quantities depend on the type and number of tests to which the material is to be subjected, and sufficient material must be obtained to provide for the proper execution of these tests. Standard control and acceptance tests are covered by ASTM Standards, and specify the portion of the field sample required for each specific test.

TABLE I

Guide for Estimating Quantity of Sample

| Maximum Nominal Size Approx. Area of Aggregate | Approximate Weight of Aggregates Uncompacted Mixture | |
|---|---|---|
| Compacted Mixture | Minimum kg (lb.) | Minimum cm$^2$ (in.$^2$) |
| 02.36-mm (No.8) | 1.8 (4) | 232 (36) |
| 04.75-mm (No.4) | 1.8 (4) | 232 (36) |
| 09.50-mm (⅜-in.) | 3.6 (8) | 232 (36) |
| 12.50-mm (½-in.) | 5.4 (12) | 413 (64) |
| 19.00-mm (¾-in.) | 7.3 (16) | 645 (100) |
| 25.00-mm (1-in.) | 9.1 (20) | 929 (144) |
| 38.10-mm (1 ½-in.) | 11.3 (25) | 929 (144) |
| 50.00-mm (2-in.) | 15.9 (35) | 1453 (225) |

Generally, the amounts specified in Table I provide adequate material for routine testing. Extract test portions are obtained from a field sample by quartering or splitting in a manner similar to Practice C 702, or as required by other applicable test methods.

Note, the approximate areas of a sample for a given weight are given in Table I. These dimensions are based on the normal laydown thickness for each aggregate size. Differences in thickness, specific gravity of the aggregate, and mix design can cause some variance in these areas.

After the preceding process is used to obtain the proper field sample, the physical size of the test sample must be reduced to a size that the test equipment can accommodate without altering its properties. In order to achieve the most representative test results, it becomes necessary to use the methods outlined in the AASHTO MATERIALS STANDARD SPECIFICATIONS FOR TRANSPORTATION MATERIALS manual.

The process of quartering involves the use of the following standard specification found on page 872 of AASHTO MATERIALS STANDARD SPECIFICATIONS FOR TRANSPORTATION MATERIALS manual (Copyright 1998 by the American Association of State Highway and Transportation Officials, 444 North Capitol Street, N.W., Suite 249 Washington, D.C. 20001).:

Quartering 9.1 Apparatus shall consist of a straightedge, scoop, shovel, or trowel, a broom or brush and a canvas blanket approximately 2 by 2.5 m (6 by 8 ft).

10.1.1 Place the original sample on a hard, clean, level surface where there will be neither loss of material nor the accidental addition of foreign material. Mix the material thoroughly by turning the entire sample over three times. With the last turning, shovel the entire sample into a conical pile by depositing each shovelful on top of the preceding one. Carefully flatten the conical pile to a uniform thickness and diameter by pressing down the apex with a shovel so that each quarter sector of the resulting pile will contain the material originally in it. The diameter should be approximately four to eight times the thickness. Divide the flattened mass into four equal quarters with a shovel or trowel and remove two diagonally opposite quarters, including all fine material, and brush the cleared spaces clean. Successively mix and quarter the remaining material until the sample is reduced to the desired size.

The purpose of the invention is to replace the above outlined, manual method to reduce the size of a large field sample of the asphalt paving mixture in a manner that mimics the approved AASHTO procedure. The advantage of the invention is that it saves time, is more accurate, and is much safer than reducing the sample by hand.

Figure 2:
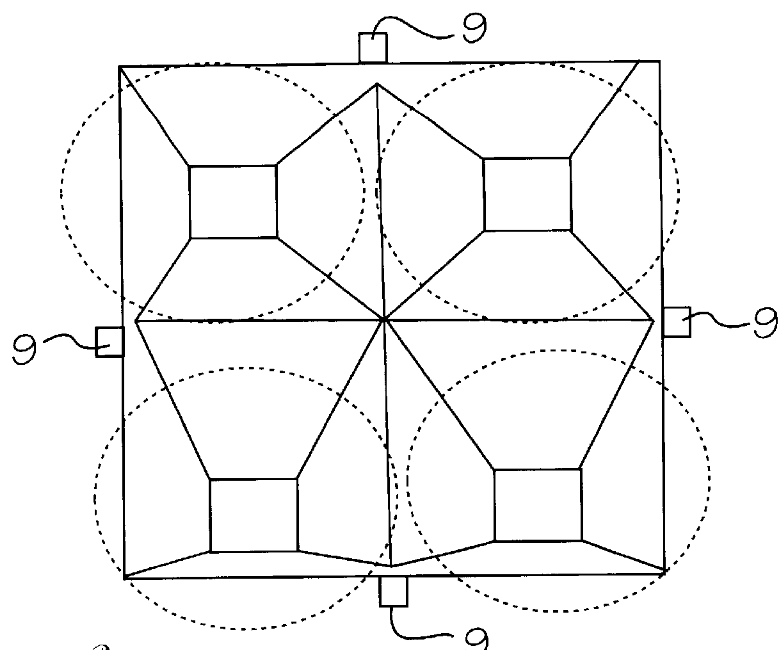
FIG. 2 depicts a top, sectional view of the apparatus shown in FIG. 1, taken along lines A—A.
Figure 3:
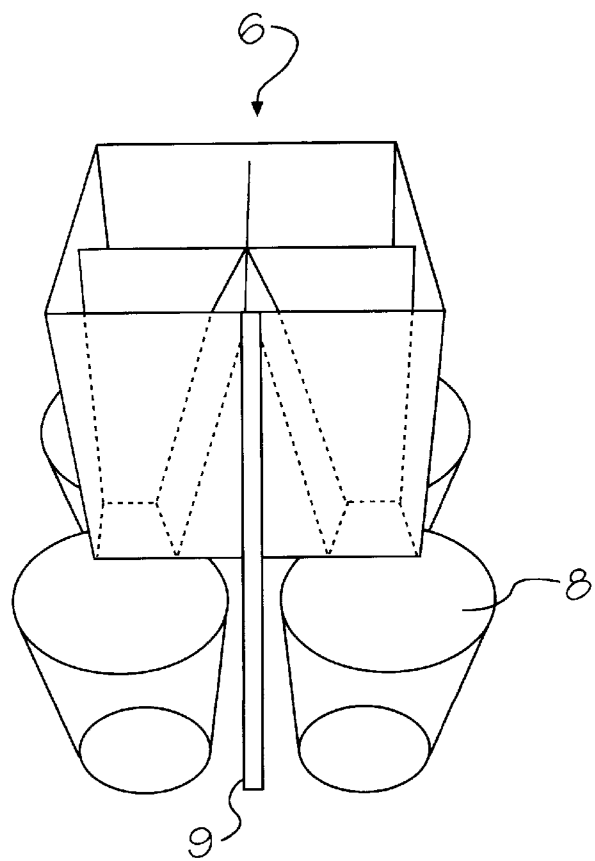
FIG. 3 shows a perspective view of the section of the apparatus disposed below lines A—A of FIG. 1.

Now referring to FIGS. 1 through 3, the separating and segregating device 10 of this invention is illustrated. The device 10 comprises a funnel 1 having a neck 12. A hopper 2 is disposed directly beneath the neck 12 of the funnel 1. Four chutes 7 are located below the hopper 2, which provide a grid configuration, best observed in FIGS. 2 and 3. Four sampling buckets 8 are arranged beneath the chutes 7. Elongated legs 9, respectively positioned on each side of the hopper 2 (best observed in FIG. 2), support the hopper 2 in relation to the buckets 8. Also disposed in hopper 2 is an interior funnel **1*a* for further directing particulate matter into the sampling buckets 8**.

The batch of particulate material is poured into the funnel, which directs the material towards the center thereof. The centering of the material assures that an even distribution of the material is presented to the hopper 2.

Four gates 3, located in the bottom of the hopper 2, are then opened by handle 4 to allow the material to fall on the grid 6 formed by the four, equally spaced chutes 7 located below the hopper 2. The handle 4, is rotated (arrow 14), causing the release tab 16 to unlatch the hopper gates 3, which drop downwardly about respective hinges 5, thus releasing the material on to the grid 6 and into the buckets 8. The gates 3 can be reset after they have been released. The handle 4 can be replaced by a solenoid (not shown), that would automatically pull the release tab 16, in order to release the gates 3.

The material passes from the hopper 2 into the grid 6, and is evenly distributed by the chutes 7 into the four awaiting, spaced-apart buckets 8. The gates 3 and the grid 6 act cooperatively to substantially separate the bulk quantity of the materials in hopper 2, into four equal segments. Reduction of the hot asphalt mix, or any other batch of particulate material, is accomplished quickly by the device 10, while closely duplicating the approved AASHTO procedure.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. A particulate sampling device, comprising:

a hopper for receiving a quantity of particulate material, said hopper comprising a plurality of releasably affixed gates for holding said quantity of particulate material in said hopper until its release;

means defining a grid disposed below said hopper to separate said quantity of particulate material into substantially equal segments after said particulate material is released by said plurality of releasably affixed gates;

means including a handle supported by said hopper for manually releasing said plurality of releasably affixed gates for releasing said particulate material onto said grid;

receiving means disposed below said grid for receiving said separated particulate material in said substantially equal segments, whereby a sample of said particulate material is obtained from one of said equally separated segments.

2. The particulate sampling device in accordance with claim 1, further comprising a funnel for directing particulate material into a center portion of said hopper.

3. The particulate sampling device in accordance with claim 1, wherein said grid further comprises a plurality of equally spaced chutes disposed below said hopper.

4. The particulate sampling device in accordance with claim 1, wherein said receiving means comprises four spaced-apart buckets.

5. The particulate sampling device in accordance with claim 2, wherein said funnel further comprises a neck portion for centering said particulate material into a center portion of said hopper.

6. A particulate sampling device, comprising:

a hopper for receiving a quantity of particulate material, said hopper comprising a plurality of releasably affixed gates for holding said quantity of particulate material in said hopper until its release;

manually controlled release means supported by said hopper for releasing said quantity of particulate material from said hopper;

means defining a grid disposed below said hopper to separate said quantity of particulate material into substantially equal segments, said grid being integrally configured with a plurality of chutes that transport separated material downwardly therefrom; and receiving means disposed below said grid and said chutes for receiving said separated particulate material in said substantially equal segments, whereby a sample of said particulate material is obtained from one of said equally separated segments.

7. The particulate sampling device in accordance with claim 6, further comprising a funnel for directing particulate material into a center portion of said hopper.

8. The particulate sampling device in accordance with claim 7, wherein said funnel further comprises a neck portion for centering said particulate material into a center portion of said hopper.

9. The particulate sampling device in accordance with claim 6, wherein said plurality of chutes are equally spaced with respect to said grid.

10. The particulate sampling device in accordance with claim 6, wherein said receiving means comprises four spaced-apart buckets.

11. A particulate sampling device, comprising:

a hopper for receiving a quantity of particulate material, said hopper comprising a plurality of releasable gates for releasing said particulate material from said hopper;

a funnel disposed adjacent said hopper for directing said quantity of particulate material into said hopper;

means defining a grid disposed below said hopper to separate said quantity of particulate material into substantially equal segments, said grid being configured with a plurality of integral chutes that transport separated material downwardly therefrom; and receiving means disposed below said grid and said chutes for receiving said separated particulate material in said substantially equal segments, whereby a sample of said particulate material is obtained from one of said equally separated segments.

12. The particulate sampling device in accordance with claim 11, wherein said funnel directs said particulate material into a center portion of said hopper.

13. The particulate sampling device in accordance with claim 11, wherein said plurality of chutes are equally spaced with respect to said grid.

14. The particulate sampling device in accordance with claim 11, wherein said receiving means comprises four spaced-apart buckets.

15. The particulate sampling device in accordance with claim 11, wherein said funnel further comprises a neck portion for centering said particulate material into a center portion of said hopper.

16. The particulate sampling device in accordance with claim 11, further comprising an interior funnel disposed in said hopper for directing said quantity of particulate matter into said plurality of chutes.

* * * * *